United States Patent
Bouchard et al.

[11] Patent Number: 6,160,135
[45] Date of Patent: Dec. 12, 2000

[54] TAXOIDS, PREPARATION THEREOF AND PHARMACEUTICAL COMPOSITIONS CONTAINING SAME

[75] Inventors: Hervé Bouchard, Thiais; Jean-Dominique Bourzat, Vincennes; Alain Commerçon, Vitry-sur-Seine, all of France

[73] Assignee: Rhone-Poulenc Rorer S.A., Antony, France

[21] Appl. No.: 09/117,659

[22] PCT Filed: Mar. 5, 1997

[86] PCT No.: PCT/FR97/00386

§ 371 Date: Aug. 4, 1998

§ 102(e) Date: Aug. 4, 1998

[87] PCT Pub. No.: WO97/32869

PCT Pub. Date: Sep. 12, 1997

[30] Foreign Application Priority Data

Mar. 6, 1996 [FR] France ................................. 96 02804

[51] Int. Cl.$^7$ ................................................ C07D 305/14
[52] U.S. Cl. ............................................ 549/510; 549/511
[58] Field of Search ..................................... 549/510, 511

[56] References Cited

FOREIGN PATENT DOCUMENTS

| | | |
|---|---|---|
| 428376 | 5/1991 | European Pat. Off. . |
| 555485 | 8/1993 | European Pat. Off. . |
| 590267 | 4/1994 | European Pat. Off. . |
| 694539 | 1/1996 | European Pat. Off. . |
| WO94/21250 | 9/1994 | WIPO . |
| WO95/11241 | 4/1995 | WIPO . |
| WO96/03394 | 2/1996 | WIPO . |

OTHER PUBLICATIONS

K.C. Nicolaou et al., "Design, Synthesis, and Biological Activity or Protaxols," *Nature*, vol. 364 (1993).

Primary Examiner—Ba K. Trinh
Attorney, Agent, or Firm—Finnegan, Henderson, Farabow, Garrett & Dunner, L.L.P.

[57] ABSTRACT

Novel taxoids of general formula (I), the preparation thereof and pharmaceutical compositions containing same, are disclosed. In general formula (I), Z is a hydrogen atom or a radical of general formula (H), wherein $R_1$ is an optionally substituted benzoyl radical or a radical $R_2$—O—CO—, where $R_2$ is an alkyl, alkenyl, alkynyl, cycloalkyl, cycloalkenyl, bicycloalkyl, optionally substituted phenyl or heterocyclyl radical; $R_3$ is an alkyl, alkenyl, alkyl, cycloalkyl, phenyl, naphthyl or aromatic heterocyclic radical; $R_4$ is a hydroxy radical or an alkoxy, alkenyloxy, optionally substituted alkynyloxy, alkanoyloxy, alkenoyloxy, alkynyloxy, alkoxyacetyl or alkyloxycarbonyloxy radical, or a cycloalkyloxy, cycloalkenyloxy, arylcarbonyloxy or heterocyclylcarbonyloxy radical; and $R_5$ is an optionally substituted alkoxy radical or a cycloalkyloxy or cycloalkenyloxy radical. The novel compounds of general formula (I), wherein Z is a radical of general formula (II), have remarkable antitumoral and antineoplastic properties.

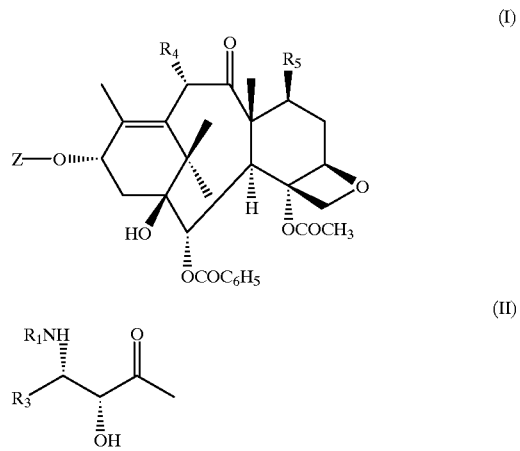

18 Claims, No Drawings

TAXOIDS, PREPARATION THEREOF AND PHARMACEUTICAL COMPOSITIONS CONTAINING SAME

This application is a 371 of PCT/FR97/00386 dated Mar. 5, 1997.

The present invention relates to new taxoids of general formula:

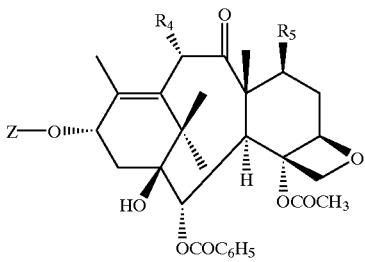

in which

Z represents a hydrogen atom or a radical of general formula:

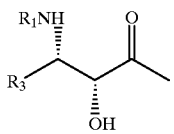

in which:

$R_1$ represents a benzoyl radical optionally substituted with one or more identical or different atoms or radicals chosen from halogen atoms and alkyl radicals containing 1 to 4 carbon atoms, alkoxy radicals containing 1 to 4 carbon atoms or trifluoromethyl radicals, thenoyl or furoyl radicals or a radical $R_2$—O—CO— in which $R_2$ represents:

an alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 10 carbon atoms, these radicals being optionally substituted with one or more substituents chosen from halogen atoms and hydroxyl radicals, alkoxy radicals containing 1 to 4 carbon atoms, dialkylamino radicals in which each alkyl portion contains 1 to 4 carbon atoms, piperidino or morpholino radicals, 1-piperazinyl radicals (optionally substituted at the 4-position with an alkyl radical containing 1 to 4 carbon atoms or with a phenylalkyl radical in which the alkyl portion contains 1 to 4 carbon atoms), cycloalkyl radicals containing 3 to 6 carbon atoms, cycloalkenyl radicals containing 4 to 6 carbon atoms, phenyl radicals (optionally substituted with one or more atoms or radicals chosen from halogen atoms and alkyl radicals containing 1 to 4 carbon atoms or alkoxy radicals containing 1 to 4 carbon atoms), cyano or carboxyl radicals or alkoxycarbonyl radicals in which the alkyl portion contains 1 to 4 carbon atoms, a phenyl or α- or β-naphthyl radical optionally substituted with one or more atoms or radicals chosen from halogen atoms and alkyl radicals containing 1 to 4 carbon atoms or alkoxy radicals containing 1 to 4 carbon atoms, or a 5-membered aromatic heterocyclic radical preferably chosen from furyl and thienyl radicals, or a saturated heterocyclic radical containing 4 to 6 carbon atoms, optionally substituted with one or more alkyl radicals containing 1 to 4 carbon atoms, $R_3$ represents an unbranched or branched alkyl radical containing 1 to 8 carbon atoms, an unbranched or branched alkenyl radical containing 2 to 8 carbon atoms, an unbranched or branched alkynyl radical containing 2 to 8 carbon atoms, a cycloalkyl radical containing 3 to 6 carbon atoms, a phenyl or α- or β-naphthyl radical optionally substituted with one or more atoms or radicals chosen from halogen atoms and alkyl, alkenyl, alkynyl, aryl, aralkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, alkylcarbamoyl, dialkylcarbamoyl, cyano, nitro and trifluoromethyl radicals, or a 5-membered aromatic heterocycle containing one or more identical or different hetero atoms chosen from nitrogen, oxygen and sulphur atoms and optionally substituted with one or more identical or different substituents chosen from halogen atoms and alkyl, aryl, amino, alkylamino, dialkylamino, alkoxycarbonylamino, acyl, arylcarbonyl, cyano, carboxyl, carbamoyl, alkylcarbamoyl, dialkylcarbamoyl or alkoxycarbonyl radicals, on the understanding that, in the substituents of the phenyl, α- or β-naphthyl and aromatic heterocyclic radicals, the alkyl radicals and the alkyl portions of the other radicals contain 1 to 4 carbon atoms, and that the alkenyl and alkynyl radicals contain 2 to 8 carbon atoms, and that the aryl radicals are phenyl or α- or β-naphthyl radicals, $R_4$ represents a hydroxyl radical or an alkoxy radical containing 1 to 6 carbon atoms in an unbranched or branched chain, an alkenyloxy radical containing 3 to 6 carbon atoms in an unbranched or branched chain, an alkynyloxy radical containing 3 to 6 carbon atoms in an unbranched or branched chain, a cycloalkyloxy radical containing 3 to 6 carbon atoms, a cycloalkenyloxy radical containing 3 to 6 carbon atoms, an alkanoyloxy radical in which the alkanoyl portion contains 2 to 6 carbon atoms in an unbranched or branched chain, an alkenoyloxy radical in which the alkenoyl portion contains 3 to 6 carbon atoms in an unbranched or branched chain, an alkynoyloxy radical in which the alkynoyl portion contains 3 to 6 carbon atoms in an unbranched or branched chain, an alkoxyacetyl radical in which the alkyl portion contains 1 to 6 carbon atoms in an unbranched or branched chain, an alkylthioacetyl radical in which the alkyl portion contains 1 to 6 carbon atoms in an unbranched or branched chain or an alkyloxycarbonyloxy radical in which the alkyl portion contains 1 to 6 carbon atoms in an unbranched or branched chain, these radicals being optionally substituted with one or more halogen atoms or with an alkoxy radical containing 1 to 4 carbon atoms, an alkylthio radical containing 1 to 4 carbon atoms or a carboxyl radical, an alkyloxycarbonyl radical in which the alkyl portion contains 1 to 4 carbon atoms, a cyano or carbamoyl radical or an N-alkylcarbamoyl or N,N-dialkylcarbamoyl radical in which each alkyl portion contains 1 to 4 carbon atoms or, with the nitrogen atom to which it is linked, forms a saturated 5- or 6-membered heterocyclic radical optionally containing a second hetero atom chosen from oxygen, sulphur and nitrogen atoms, optionally substituted with an alkyl radical containing 1 to 4 carbon atoms or a phenyl radical or a phenylalkyl radical in which the alkyl portion contains 1 to 4 carbon atoms, or alternatively $R_4$ represents a carbamoyloxy radical or an N-alkylcarbamoyloxy radical in which the alkyl portion contains 1 to 4 carbon atoms, an N,N-dialkylcarbamoyloxy radical in which each alkyl portion contains 1 to 4 carbon atoms or a benzoyloxy radical or a heterocyclylcarbonyloxy radical in which radical the heterocyclic portion represents a 5- or 6-membered aromatic heterocycle containing one or more hetero atoms chosen from oxygen, sulphur and nitrogen atoms, $R_5$ represents an alkoxy radical containing 1 to 6 carbon atoms in an unbranched or branched chain optionally substituted with an alkoxy radical containing 1 to 4 carbon atoms, an alkenyloxy radical containing 3 to 6 carbon atoms, an alkynyloxy radical containing 3 to 6 carbon atoms, a cycloalkyloxy radical containing 3 to 6 carbon atoms, a cycloalkenyloxy radical containing 3 to 6 carbon atoms, these radicals being optionally substituted with one or more halogen atoms or with an alkoxy radical containing 1 to 4 carbon atoms, an alkylthio radical containing 1 to 4 carbon atoms or a carboxyl radical, an alkyloxycarbonyl radical in which the alkyl portion contains 1 to 4 carbon atoms, a cyano or carbamoyl radical or an N-alkylcarbamoyl or N,N-dialkylcarbamoyl radical in which each alkyl portion contains 1 to 4 carbon atoms or, with the nitrogen atom to which it is linked, forms a saturated 5- or 6-membered heterocyclic radical optionally containing a second hetero atom chosen from oxygen, sulphur and nitrogen atoms, optionally substituted with an alkyl radical containing 1 to 4 carbon atoms or a phenyl radical or a phenylalkyl radical in which the alkyl portion contains 1 to 4 carbon atoms.

Preferably, the aryl radicals which can be represented by $R_3$ are phenyl or α- or β-naphthyl radicals optionally substituted with one or more atoms or radicals chosen from halogen atoms (fluorine, chlorine, bromine, iodine) and alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, dialkylcarbamoyl, cyano, nitro and trifluoromethyl radicals, on the understanding that the alkyl radicals and the alkyl portions of the other radicals contain 1 to 4 carbon atoms, that the alkenyl and alkynyl radicals contain 2 to 8 carbon atoms and that the aryl radicals are phenyl or α- or β-naphthyl radicals.

Preferably, the heterocyclic radicals which can be represented by $R_3$ are 5-membered aromatic heterocyclic radicals containing one or more identical or different atoms chosen from nitrogen, oxygen and sulphur atoms, optionally substituted with one or more identical or different substituents chosen from halogen atoms (fluorine, chlorine, bromine, iodine) and alkyl radicals containing 1 to 4 carbon atoms, aryl radicals containing 6 to 10 carbon atoms, alkoxy radicals containing 1 to 4 carbon atoms, aryloxy radicals containing 6 to 10 carbon atoms, amino radicals, alkylamino radicals containing 1 to 4 carbon atoms, dialkylamino radicals in which each alkyl portion contains 1 to 4 carbon atoms, acylamino radicals in which the acyl portion contains 1 to 4 carbon atoms, alkoxycarbonylamino radicals containing 1 to 4 carbon atoms, acyl radicals containing 1 to 4 carbon atoms, arylcarbonyl radicals in which the aryl portion contains 6 to 10 carbon atoms, cyano, carboxyl or carbamoyl radicals, alkylcarbamoyl radicals in which the alkyl portion contains 1 to 4 carbon atoms, dialkylcarbamoyl radicals in which each alkyl portion contains 1 to 4 carbon atoms or alkoxycarbonyl radicals in which the alkoxy portion contains 1 to 4 carbon atoms.

Preferably, the radical $R_4$ represents a hydroxyl radical or an unbranched or branched alkoxy radical containing 1 to 6 carbon atoms or an alkanoyloxy radical containing 2 to 6 carbon atoms optionally substituted with a methoxy, ethoxy, methylthio, ethylthio, carboxyl, methoxycarbonyl, ethoxycarbonyl, cyano, carbamoyl, N-methylcarbamoyl, N-ethylcarbamoyl, N,N-dimethylcarbamoyl, N,N-diethylcarbamoyl, N-pyrrolidinocarbonyl or N-piperidinocarbonyl and $R_5$ represents an unbranched or branched alkoxy radical containing 1 to 6 carbon atoms.

More especially, the present invention relates to the products of general formula (I) in which Z represents a hydrogen atom or a radical of general formula (II) in which $R_1$ represents a benzoyl radical or a radical $R_2$—O—CO— in which $R_2$ represents a tert-butyl radical and $R_3$ represents an alkyl radical containing 1 to 6 carbon atoms, an alkenyl radical containing 2 to 6 carbon atoms, a cycloalkyl radical containing 3 to 6 carbon atoms, a phenyl radical optionally substituted with one or more identical or different atoms or radicals chosen from halogen atoms (fluorine, chlorine) and alkyl (methyl), alkoxy (methoxy), dialkylamino (dimethylamino), acylamino (acetylamino), alkoxycarbonylamino (tert-butoxycarbonylamino) and trifluoromethyl radicals, or a 2- or 3-furyl, 2- or 3-thienyl or 2-, 4- or 5-thiazolyl radical, and $R_4$ represents a hydroxyl radical or an unbranched or branched alkyloxy radical containing 1 to 6 carbon atoms or an alkanoyloxy radical containing 2 to 6 carbon atoms and $R_5$ represents an unbranched or branched alkyloxy radical containing 1 to 6 carbon atoms.

Still more especially, the present invention relates to the products of general formula (I) in which Z represents a hydrogen atom or a radical of general formula (II) in which $R_1$ represents a benzoyl radical or a radical $R_2$—O—CO— in which $R_2$ represents a tert-butyl radical and $R_3$ represents an isobutyl, isobutenyl, butenyl, cyclohexyl, phenyl, 2-furyl, 3-furyl, 2-thienyl, 3-thienyl, 2-thiazolyl, 4-thiazolyl or 5-thiazolyl radical, $R_4$ represents a hydroxyl radical or a methoxy, ethoxy or propoxy radical and $R_5$ represents a methoxy radical.

The products of general formula (I) in which Z represents a radical of general formula (II) display noteworthy antitumour and antileukaemic properties.

According to the present invention, the new products of general formula (I) in which Z represents a radical of general formula (II) may be obtained by esterification of a product of general formula:

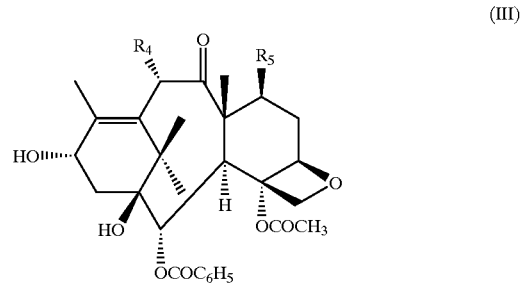

(III)

in which $R_4$ and $R_5$ are defined as above, by means of an acid of general formula:

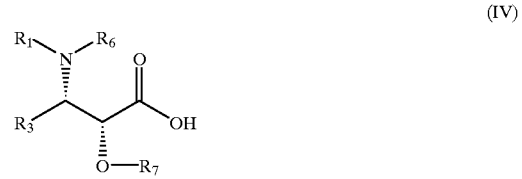

(IV)

in which $R_1$ and $R_3$ are defined as above, and either $R_6$ represents a hydrogen atom and $R_7$ represents a group protecting the hydroxyl function, or $R_6$ and $R_7$ together form a saturated 5- or 6-membered heterocycle, or of a derivative of this acid, to obtain an ester of general formula:

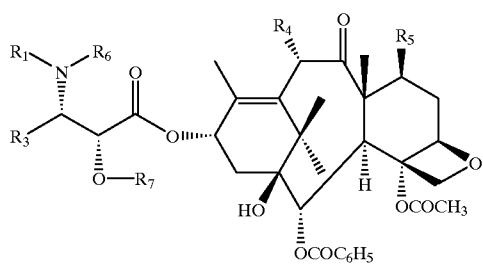

(V)

in which $R_1$, $R_3$, $R_4$, $R_5$, $R_6$ and $R_7$ are defined as above, followed by the replacement of the protective groups represented by $R_7$ and/or $R_6$ and $R_7$ with hydrogen atoms.

To obtain a product of general formula (I) in which $R_4$ represents a hydroxyl radical, it is advantageous to protect the hydroxyl function at the 10-position of the product of general formula (III), prior to the esterification, in the form, for example, of an alkoxyacetoxy radical and then to replace the protective group at the 10-position with a hydroxyl radical by means, for example, of hydrazine hydrate and the protective groups $R_7$ and/or $R_6$ and $R_7$ with hydrogen atoms.

The esterification by means of an acid of general formula (IV) may be carried out in the presence of a condensing agent (reactive carbonate, carbodiimide) and of an activating agent (aminopyridines) in an organic solvent (ether, ester, ketones, nitrites, aliphatic hydrocarbons, halogenated aliphatic hydrocarbons, aromatic hydrocarbons) at a temperature of between −10 and 90° C.

The esterification may also be performed using the acid of general formula (IV) in the form of a symmetric anhydride, working in the presence of an activating agent (aminopyridines), in an organic solvent (ethers, esters, ketones, nitriles, aliphatic hydrocarbons, halogenated aliphatic hydrocarbons, aromatic hydrocarbons) at a temperature of between 0 and 90° C.

The esterification may also be performed using the acid of general formula (IV) in the form of a halide or in the form of a mixed anhydride with an aliphatic or aromatic acid, optionally prepared in situ, in the presence of a base (tertiary aliphatic amine), working in an organic solvent (ethers, esters, ketones, nitriles, aliphatic hydrocarbons, halogenated aliphatic hydrocarbons, aromatic hydrocarbons) at a temperature of between 0 and 80° C.

Preferably, $R_6$ represents a hydrogen atom and $R_7$ represents a group protecting the hydroxyl function or $R_6$ and $R_7$ together form a saturated 5- or 6-membered heterocycle.

When $R_6$ represents a hydrogen atom, $R_7$ preferably represents a methoxymethyl, 1-ethoxyethyl, benzoyloxymethyl, trimethylsilyl, triethylsilyl, β-trimethylsilylethoxymethyl, benzoyloxycarbonyl or tetrahydropyranyl radical.

When $R_6$ and $R_7$ together form a heterocycle, the latter is preferably an oxazolidine ring optionally mono-substituted or gem-disubstituted at the 2-position.

The replacement of the protective groups $R_7$ and/or $R_6$ and $R_7$ with hydrogen atoms may be carried out, depending on their nature, in the following manner:

1) When $R_6$ represents a hydrogen atom and $R_7$ represents a group protecting the hydroxyl function, the replacement of the protective groups with hydrogen atoms is carried out by means of an inorganic acid (hydrochloric acid, sulphuric acid, hydrofluoric acid) or an organic acid (acetic acid, methanesulphonic acid, trifluoromethanesulphonic acid, p-toluenesulphonic acid), used alone or in the form of a mixture, working in an organic solvent chosen from alcohols, ethers, esters, aliphatic hydrocarbons, halogenated aliphatic hydrocarbons, aromatic hydrocarbons and nitrites, at a temperature of between −10 and 60° C., or by means of a source of fluoride ions such as a hydrofluoric acid-triethylamine complex or by catalytic hydrogenation, 2) When $R_6$ and $R_7$ together form a saturated 5- or 6-membered heterocycle and more particularly an oxazolidine ring of general formula:

(VI)

in which $R_1$ is defined as above, $R_8$ and $R_9$, which are identical or different, represent a hydrogen atom or an alkyl radical containing 1 to 4 carbon atoms, or an aralkyl radical in which the alkyl portion contains 1 to 4 carbon atoms and the aryl portion preferably represents a phenyl radical optionally substituted with one or more alkoxy radicals containing 1 to 4 carbon atoms, or an aryl radical preferably representing a phenyl radical optionally substituted with one or more alkoxy radicals containing 1 to 4 carbon atoms, either $R_8$ represents an alkoxy radical containing 1 to 4 carbon atoms or a trihalomethyl radical such as trichloromethyl or a phenyl radical substituted with a trihalomethyl radical such as trichloromethyl and $R_9$ represents a hydrogen atom, or $R_8$ and $R_9$ together form, with the carbon atom to which they are linked, a ring having 4 to 7 members, the replacement of the protective group formed by $R_6$ and $R_7$ with hydrogen atoms may be carried out, according to the meanings of $R_1$, $R_8$ and $R_9$, in the following manner:

a) When $R_1$ represents a tert-butoxycarbonyl radical, $R_8$ and $R_9$, which are identical or different, represent an alkyl radical or an aralkyl (benzyl) or aryl (phenyl) radical, either $R_8$ represents a trihalomethyl radical or a phenyl radical substituted with a trihalomethyl radical, and $R_9$ represents a hydrogen atom, or $R_8$ and $R_9$ together form a 4- to 7-membered ring, the treatment of the ester of general formula (V) with an inorganic or organic acid, optionally in an organic solvent such as an alcohol, gives the product of general formula:

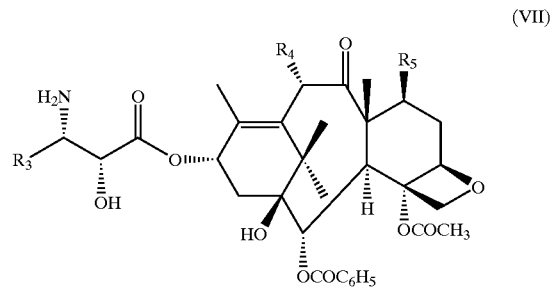

(VII)

in which $R_3$, $R_4$ and $R_5$ are defined as above, which is acylated by means of benzoyl chloride in which the phenyl ring is optionally substituted, thenoyl chloride, furoyl chloride or a product of general formula:

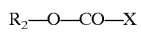
$$R_2\text{—}O\text{—}CO\text{—}X \qquad (VIII)$$

in which $R_2$ is defined as above and X represents a halogen atom (fluorine, chlorine) or a residue —O—$R_2$ or —O—CO—O—$R_2$, to obtain a product of general formula (I) in which Z represents a radical of general formula (II).

Preferably, the product of general formula (V) is treated with formic acid at a temperature in the region of 20° C., to give the product of general formula (VII).

Preferably, the acylation of the product of general formula (VII) by means of benzoyl chloride in which the phenyl radical is optionally substituted, thenoyl chloride or furoyl chloride or a product of general formula (VIII) is carried out in an inert organic solvent chosen from esters such as ethyl acetate, isopropyl acetate or n-butylacetate and halogenated aliphatic hydrocarbons such as dichloromethane or 1,2-dichloroethane in the presence of an inorganic base such as sodium bicarbonate or an organic base such as triethylamine. The reaction is carried out at a temperature of between 0 and 50° C., preferably in the region of 20° C.

b) When $R_1$ represents an optionally substituted benzoyl radical, a thenoyl or furoyl radical or a radical $R_2O$—CO— in which $R_2$ is defined as above, $R_8$ represents a hydrogen atom or an alkoxy radical containing 1 to 4 carbon atoms or a phenyl radical substituted with one or more alkoxy radicals containing 1 to 4 carbon atoms and $R_9$ represents a hydrogen atom, the replacement of the protective group formed by $R_6$ and $R_7$ with hydrogen atoms is carried out in the presence of an inorganic acid (hydrochloric acid, sulphuric acid) or an organic acid (acetic acid, methanesulphonic acid, trifluoromethanesulphonic acid, p-toluenesulphonic acid), used alone or in the form of a mixture, in a stoichiometric or catalytic quantity, working in an organic solvent chosen from alcohols, ethers, esters, aliphatic hydrocarbons, halogenated aliphatic hydrocarbons and aromatic hydrocarbons at a temperature of between –10 and 60° C., preferably between 15 and 30° C.

According to the invention, the products of general formula (I) in which $R_4$ and $R_5$ are defined as above, R4 not being capable of represents a hydroxyl radical and Z represents a hydrogen atom or a radical of general formula (II) may be obtained by the action of a product of general formula:

$$R'_4\text{—}X_1 \qquad (IX)$$

in which $R'_4$ is such that $R'_4$—O is identical to $R_4$ defined as above and $X_1$ represents a halogen atom, on a product of general formula:

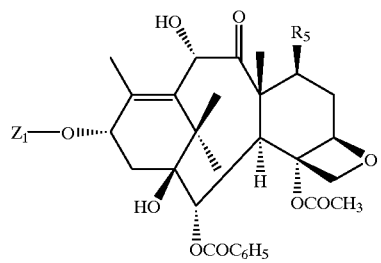
(X)

in which $R_5$ is defined as above and $Z_1$ represents a hydrogen atom or a group protecting the hydroxyl function or a radical of general formula:

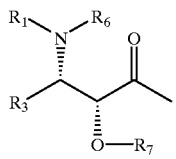
(XI)

in which $R_1$, $R_3$, $R_6$ and $R_7$ are defined as above, optionally followed by the replacement of the protective groups with hydrogen atoms.

Generally, the action of the product of general formula (IX) on a product of general formula (X) is carried out, after metalation of the hydroxyl function at the 10-position by means of an alkali metal hydride such as sodium hydride, an alkali metal amide such as lithium amide or an alkali metal alkylide such as butyllithium, working in an organic solvent such as dimethylformamide or tetrahydrofuran, at a temperature of between 0 and 50° C.

When $Z_1$ represents a group protecting the hydroxyl function, this group is preferably a silylated radical, such as a trialkylsilyl radical, whose replacement with a hydrogen atom is carried out by means of an acid such as hydrofluoric acid or trifluoroacetic acid, in the presence of a base such as triethylamine or pyridine optionally substituted with one or more alkyl radicals containing 1 to 4 carbon atoms, optionally combined with an inert organic solvent such as a nitrile such as acetonitrile or a halogenated aliphatic hydrocarbon such as dichloromethane, at a temperature of between 0 and 80° C.

When $Z_1$ represents a radical of general formula (XI), the replacement of the protective groups $R_6$ and/or $R_6$ and $R_7$ with hydrogen atoms is carried out under the conditions described above for the replacement of the protective groups of the product of general formula (V).

The product of general formula (X) may be obtained by reduction of a product of general formula:

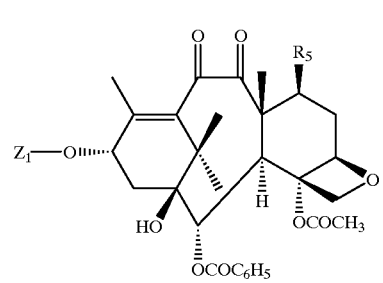
(XII)

in which $R_5$ and $R_1$ are defined as above.

Generally, the reducing agent is chosen from aluminohydrides or borohydrides such as alkali or alkaline-earth metal borohydrides such as sodium borohydride, in the presence of an aliphatic alcohol containing 1 to 4 carbon atoms such as methanol, the reduction being performed at a temperature of between 0° and 50° C., preferably in the region of 20° C.

The product of general formula (XII) may be obtained by the action of an oxidizing agent on a product of general formula:

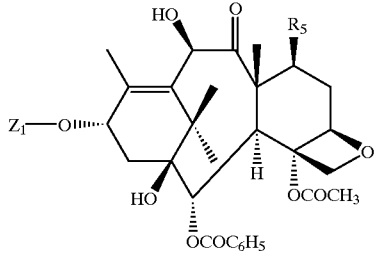

(XIII)

in which $R_5$ and $Z_1$ are defined as above.

Generally, the oxidizing agent is chosen from agents which make it possible to oxidize the secondary alcohol function without affecting the rest of the molecule, such as for example oxygen, ammonium perruthenate, manganese dioxide, copper acetate or pyridinium chlorochromate, working in an organic solvent such as optionally halogenated aliphatic hydrocarbons such as dichloromethane, at a temperature of between 0 and 50° C., preferably in the region of 25° C.

The product of general formula (XIII) may be obtained by the action of hydrazine, preferably in hydrate form, on a product of general formula:

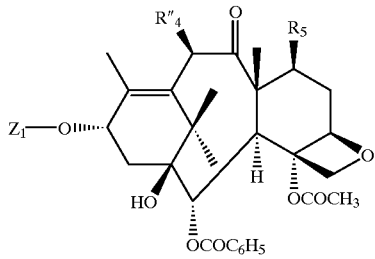

(XIV)

in which $Z_1$ and $R_5$ are defined as above and $R''_4$ represents an alkoxyacetoxy or alkylthioacetoxy radical in which the alkyl portion contains 1 to 4 carbon atoms.

Generally, the reaction is carried out working in an aliphatic alcohol containing 1 to 4 carbon atoms such as ethanol, at a temperature of between 0 and 50° C.

The product of general formula (XIV) may be obtained by the action of activated Raney nickel, in the presence of an aliphatic alcohol containing 1 to 3 carbon atoms, on a product of general formula:

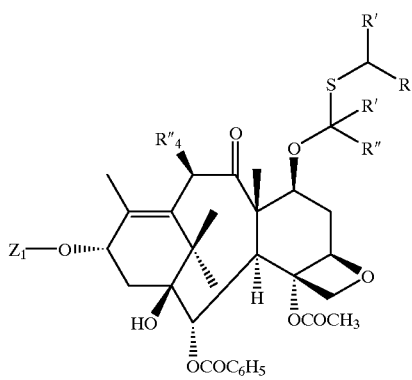

(XV)

in which $Z_1$ and $R''_4$ are defined as above, R' and R", which are identical or different, represent a hydrogen atom or an alkyl radical containing 1 to 6 carbon atoms, an alkenyl radical containing 2 to 6 carbon atoms, an alkynyl radical containing 2 to 6 carbon atoms, a cycloalkyl radical containing 3 to 6 carbon atoms or a cycloalkenyl radical containing 3 to 6 carbon atoms, or R' and R" together form, with the carbon atom to which they are linked, a cycloalkyl radical containing 3 to 6 carbon atoms or a cycloalkenyl radical containing 4 to 6 carbon atoms.

Generally, the action of the activated Raney nickel in the presence of the aliphatic alcohol is carried out at a temperature of between −10 and 60° C.

The product of general formula (XV) may be obtained by the action of a dialkyl sulphoxide of general formula:

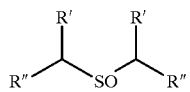

(XVI)

in which R' and R" are defined as above, on a product of general formula:

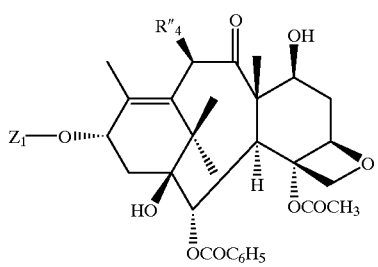

(XVII)

in which $Z_1$ and $R''_4$ are defined as above.

Generally, the reaction of the sulphoxide of general formula (XVI), preferably dimethyl sulphoxide, on the product of general formula (XVII) is carried out in the presence of a mixture of acetic acid and acetic anhydride or of a derivative of acetic acid such as a haloacetic acid, at a temperature of between 0 and 50° C., preferably in the region of 25° C.

The product of general formula (XVII) may be obtained by the action, for example, of a triethylamine-hydrofluoric acid complex, on a product of general formula:

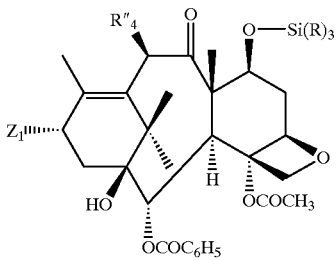

(XVIII)

in which $Z_1$ and $R''_4$ are defined as above.

Generally, the reaction is carried out working in an organic solvent such as an optionally halogenated aliphatic hydrocarbon, at a temperature of between −25 and 25° C.

The product of general formula (XVIII) may be obtained under the conditions described in international patent PCT WO 95/11241.

The new products of general formula (I) obtained by carrying out the processes according to the invention may be purified according to known methods such as crystallization or chromatography.

The products of general formula (I) in which Z represents a radical of general formula (II) display noteworthy biological properties.

In vitro, measurement of the biological activity is performed on tubulin extracted from pig's brain by the method of M. L. Shelanski et al., Proc. Natl. Acad. Sci. USA, 70, 765–768 (1973). Study of the depolymerization of microtubules into tubulin is performed according to the method of G. Chauviere et al., C. R. Acad. Sci., 293, series II, 501–503 (1981). In this study, the products of general formula (I) in which Z represents a radical of general formula (II) were shown to be at least as active as Taxol and Taxotere.

In vivo, the products of general formula (I) in which Z represents a radical of general formula (II) were shown to be active in mice grafted with B16 melanoma at doses of between 1 and 10 mg/kg administered intraperitoneally, as well as on other liquid or solid tumours.

The new products have antitumour properties, and more especially activity against tumours which are resistant to Taxol® or to Taxotere®. Such tumours comprise colon tumours which have a high expression of the mdr 1 gene (multiple drug resistance gene). Multiple drug resistance is a customary term relating to the resistance of a tumour to different products having different structures and mechanisms of action. Taxoids are generally known to be strongly recognized by experimental tumours such as P388/DOX, a cell line selected for its resistance to doxorubicin (DOX) which expresses mdr 1.

The example which follows illustrates the present invention.

EXAMPLE 1

35 mg of 4α-acetoxy-2α-benzoyloxy-5β,20-epoxy-1β,10α-dihydroxy-7β-methoxy-9-oxo-11-taxen-13α-yl (2R,4S,5R)-3-tert-butoxycarbonyl-2-(4-methoxyphenyl)-4-phenyl-1,3-oxazolidine-5-carboxylate is dissolved in 0.74 cm³ of a 0.1N hydrochloric acid ethanolic solution containing 1% of water. The solution thus obtained was stirred for 2 hours at a temperature in the region of 20° C. and then supplemented with 1 cm³ of a saturated aqueous sodium hydrogen carbonate solution and 3 cm³ of dichloromethane. The mixture was stirred for 5 minutes at a temperature in the region of 20° C. and separated by decantation of the organic phase. The aqueous phase was reextracted two times with 3 cm³ of dichloromethane. The organic phases were pooled, dried over magnesium sulphate, filtered and concentrated to dryness under reduced pressure (2.7 kPa) at 40° C. 34 mg of a white foam were obtained which were purified by chromatography on silica gel plates [(gel 1 mm thick, 1 plate of 20×20 cm, eluent, dichloromethane/methanol (95-5 by volume)]. After locating, using UV rays, the zone corresponding to the desired product adsorbed, this zone was scraped off and the silica recovered was washed on sintered glass 10 times with 2 cm³ of ethyl acetate. The filtrates were pooled and concentrated to dryness 5 under reduced pressure (2.7 kPa) at 20° C. 22 mg of 4α-acetoxy-2α-benzoyloxy-5β,20-epoxy-1β,10α-dihydroxy-7β-methoxy-9-oxo-11-taxen-13α-yl (2R,3S)-3-tert-butoxycarbonylamino-2-hydroxy-3-phenylpropionate were thereby obtained in the form of a white foam, the characteristics of which were as follows:

—¹H NMR spectrum (400 MHz; CDCl₃; chemical shifts δ in ppm; coupling constants J in Hz):1.13 (s, 3H:—CH₃ at position 16 or 17); 1.27 (s, 3H:—CH₃ at position 16 or 17); 1.38 [s, 9H:—C(CH₃)₃]; 1.72 (s, 3H:—CH₃); 1.76 (s, 1H:OH at position 1); 1.82 and 2.75 (2 mts, 1H each:—CH₂— at position 6); 2.08 (s, 3H:—CH₃); 2.28 and 2.35 (2 dd, J=16 and 9, 1H each:—CH₂— at position 14; 2.40 (s, 3H:—COCH₃); 2.71 (d, J=2, 1H:—OH at position 10); 3.30 (s, 3H:—OCH₃); 3.42 (broad s, 1H:—OH at position 2'); 4.20 and 4.32 (2 d, J=8.5, 1H each:—CH₂— at position 20); 4.27 (d, J=7.5, 1H:—H at position 3); 4.31 (mt, 1H:—H at position 7); 4.64 (mt, 1H:—H at position 2'); 5.02 (broad d, J=10, 1H: —H at position 5); 5.21 (mt, 1H:—H at position 10); 5.32 (broad d, J=10, 1H:—H at position 3'); 5.48 (d, J=10, 1H:—CONH—); 5.65 (d, J=7.5, 1H:—H at position 2); 6.18 (broad t, J=9, 1H:—H at position 13); from 7.25 to 7.45 (mt, 5H:—C₆H₅ at position 3'); 7.52 [t, J=7.5, 2H:—OCOC₆H₅ (—H at position 3 and H at position 5)]; 7.63 [t, J=7.5, 1H:—OCOC₆H₅ (—H at position 4)]; 8.13 [d, J=7.5, 2H:—OCOC₆H₅ (—H at position 2 and H at position 6)].

4α-acetoxy-2α-benzoyloxy-5β,20-epoxy-1β,10α-dihydroxy-7β-methoxy-9-oxo-11-taxen-13α-yl (2R,4S,5R)-3-tert-butoxycarbonyl-2-(4-methoxyphenyl)-4-phenyl-1,3-oxazolidine-5-carboxylate may be prepared in the following manner:

9 mg of sodium tetrahydruroborate were added, at a temperature in the region of 20° C., to a solution of 45 mg of 4α-acetoxy-2α-benzoyloxy-5β,20-epoxy-1β-hydroxy-7β-methoxy-9,10-dioxo-11-taxen-13α-yl (2R,4S,5R)-3-tert-butoxycarbonyl-2-(4-methoxyphenyl)-4-phenyl-1,3-oxazolidine-5-carboxylate in 2 cm³ of anhydrous ethanol, maintained under an argon atmosphere and with stirring, and the reaction mixture was maintained stirring for 1 hour at a temperature in the region of 20° C. and then 1 cm³ of distilled water was added and the mixture was stirred for 5 minutes at 20° C. 3 cm³ of dichloromethane were added and the organic phase was separated by decantation. The aqueous phase was reextracted with twice 3 cm³ of dichloromethane. The organic phases were pooled, dried over magnesium sulphate, filtered on sintered glass and concentrated to dryness under reduced pressure (2.7 kPa) at 40° C. A white foam was obtained which is purified by chromatography on a silica gel plate [(gel 1 mm thick, 1 plate of 20×20 cm, eluent: dichloromethane/methanol (95-5 by volume)]. After locating, using UV rays, the zone corresponding to the desired product adsorbed, this zone was scraped off and the silica recovered is washed on sintered glass 10 times with 2 cm³ of ethyl acetate. The filtrates were pooled and concentrated to dryness under reduced pressure (2.7 kPa) at 20° C. 22.5 mg of 4α-acetoxy-2α-benzoyloxy-5β,20-epoxy-1β,10α-dihydroxy-7β-methoxy-9-oxo-11-taxen-13α-yl (2R,4S,5R)-3-tert-butoxycarbonyl-2-(4-methoxyphenyl)-4-phenyl-1,3-oxazolidine-5-carboxylate are thereby obtained in the form of a white foam.

4α-acetoxy-2α-benzoyloxy-5β,20-epoxy-1β-hydroxy-7β-methoxy-9,10-dioxo-11-taxen-13α-yl (2R,4S,5R)-3-tert-butoxycarbonyl-2-(4-methoxyphenyl)-4-phenyl-1,3-oxazolidine-5-carboxylate were be prepared in the following manner:

500 mg of a 4 Å molecular sieve powder and 43 mg of pyridinium chlorochromate were successively added, at a temperature in the region of 20° C., to a solution of 100 mg of 4α-acetoxy-2α-benzoyloxy 5β,20-epoxy-1β,10β-dihydroxy-7β-methoxy-9-oxo-11-taxen-13α-yl (2R,4S,5R)-3-tert-butoxycarbonyl-2-(4-methoxyphenyl)-4-phenyl-1,3-oxazolidine-5-carboxylate in 5 cm³ of dichloromethane, maintained under an argon atmosphere and with stirring. The suspension obtained was stirred for 21 hours at a temperature in the region of 20° C. and then filtered on sintered glass coated with celite. The sintered glass was washed 3 times with 5 cm³ of dichloromethane. The filtrates were pooled and supplemented with powdered animal charcoal and then filtered on sintered glass and concentrated to dryness under reduced pressure (2.7 kPa) at 40° C. A yellow foam was thereby obtained which is purified by chromatography on a silica gel plate [(gel 1 mm thick, 1 plate of 20×20 cm, eluent: dichloromethane/methanol (95-5 by volume)]. After locating, using UV rays, the zone corresponding to the desired product adsorbed, this zone was scraped off and the silica recovered was washed on sintered glass 10 times with 5 cm³ of ethyl acetate. The filtrates were pooled and concentrated to dryness under reduced pressure (2.7 kPa) at 20° C. 47 mg of 4α-acetoxy-2α-benzoyloxy-5β,20-epoxy-1β-hydroxy-7β-methoxy-9,10-dioxo-11-taxen-13α-yl (2R,4S,5R) -3-tert-butoxycarbonyl-2-(4-methoxyphenyl)-4-phenyl-1,3-oxazolidine-5-carboxylate were thereby obtained in the form of a light beige foam.

4α-acetoxy-2α-benzoyloxy-5β,20-epoxy-1β,10β-dihydroxy-7β-methoxy-9-oxo-11-taxen-13α-yl (2R,4S,5R)-3-tert-butoxycarbonyl-2-(4-methoxyphenyl)-4-phenyl-1,3-oxazolidine-5-carboxylate were prepared in the following manner:

0.263 cm³ of hydrazine monohydrate was added dropwise, and at a temperature in the region of 20° C., to a solution of 150 mg of 4α-acetoxy-2α-benzoyloxy- 5β,20-epoxy-1β-hydroxy-7β-methoxy-10β-methoxyacetoxy-9-oxo-11-taxen-13α-yl (2R,4S,5R)-3-tert-butoxycarbonyl-2-(4-methoxyphenyl)-4-phenyl-1,3-oxazolidine-5-carboxylate in 4 cm³ of anhydrous ethanol, maintained under an argon atmosphere and with stirring. The reaction medium was maintained stirring for 1 hour at a temperature in the region of 20° C. and then poured into a mixture of 100 cm³ of ethyl acetate and 50 cm³ of distilled water. The organic phase was separated by decantation and the aqueous phase was reextracted 2 times with 50 cm³ of ethyl acetate. The organic phases were pooled, washed 4 times with 50 cm³ of distilled water, dried over magnesium sulphate, filtered and concentrated to dryness under reduced pressure (2.7 kPa) at 40° C. 180 mg of a white foam were obtained which were purified by chromatography on silica gel plates [gel 1 mm thick, 20×20 cm plates, eluent: dichloromethane/ ethanol (90-10 by volume)] in 90-mg fractions (2 plates). After locating, using UV rays, the zone corresponding to the desired product adsorbed, this zone was scraped off and the silica recovered was washed on sintered glass 10 times with 10 cm³ of ethyl acetate. The filtrates were pooled and concentrated to dryness under reduced pressure (2.7 kPa) at 40° C. 113 mg of 4α-acetoxy-2α-benzoyloxy-5β,20-epoxy-1β,10β-dihydroxy-7β-methoxy-9-oxo-11-taxen-13α-yl (2R, 4S,5R)-3-tert-butoxycarbonyl-2-(4-methoxyphenyl)-4-phenyl-1,3-oxazolidine-5-carboxylate were thereby obtained in the form of a white foam.

4α-acetoxy-2α-benzoyloxy-5β,20-epoxy-1β-hydroxy-7β-methoxy-10β-methoxyacetoxy-9-oxo-11-taxen-13α-yl (2R,4S,5R)-3-tert-butoxycarbonyl-2-(4-methoxyphenyl)-4-phenyl-1,3-oxazolidine-5-carboxylate were prepared in the following manner:

100 cm³ of an ethanolic suspension of activated Raney nickel (obtained from 80 cm³ of an aqueous commercial suspension at about 50%, by successive washes, up to a pH in the region of 7, with 15 times 100 cm³ of distilled water and 4 times with 150 cm³ of ethanol) were added, at a temperature in the region of 20° C., to a solution of 1.041 g of 4α-acetoxy-2α-benzoyloxy-5β,20-epoxy-1β-hydroxy-10β-methoxyacetoxy-7β-methylthiomethoxy-9-oxo-11-taxen-13α-yl (2R,4S,5R)-3-tert-butoxycarbonyl-2-(4-methoxyphenyl)-4-phenyl-1,3-oxazolidine-5-carboxylate in 100 cm³ of anhydrous ethanol, maintained under an argon atmosphere and with stirring. The reaction medium was maintained stirring for 7 days at a temperature in the region of 20° C. and then filtered on sintered glass. The sintered glass was washed 3 times with 100 cm³ of ethanol, the filtrates were pooled and concentrated to dryness under reduced pressure (2.7 kPa) at 40° C. 821 mg of a white foam were obtained which are purified by chromatography on 75 g of silica (0.063–0.2 mm) contained in a column 2.5 cm in diameter [eluent: dichloromethane/ethyl acetate (90-10 by volume)], collecting 5-cm³ fractions. The fractions containing only the desired product were pooled and concentrated to dryness under reduced pressure (2.7 kPa) at 40° C. 228 mg of 4α-acetoxy-2α-benzoyloxy-5β,20-epoxy-1β-hydroxy-7β-methoxy-10β-methoxyacetoxy-9-oxo-11-taxen-13α-yl (2R,4S,5R)-3-tert-butoxycarbonyl-2-(4-methoxyphenyl)-4-phenyl-1,3-oxazolidine-5-carboxylate were thereby obtained in the form of a white foam.

4α-acetoxy-2α-benzoyloxy-5,20-epoxy-1β-hydroxy-10β-methoxyacetoxy-7β-methylthiomethoxy-9-oxo-11-taxen-13α-yl (2R,4S,5R)-3-tert-butoxycarbonyl-2-(4-methoxyphenyl)-4-phenyl-1,3-oxazolidine-5-carboxylate were prepared in the following manner:

3.35 cm³ of acetic acid and 11.5 cm³ of acetic anhydride were added, at a temperature in the region of 20° C., to a solution of 5 g of 4α-acetoxy-2α-benzoyloxy-5β,20-epoxy-1β,7β-dihydroxy-10β-methoxyacetoxy-9-oxo-11-taxen-13α-yl (2R,4S,5R)-3-tert-butoxycarbonyl-2-(4-methoxyphenyl)-4-phenyl-1,3-oxazolidine-5-carboxylate in 165 cm³ of anhydrous dimethyl sulphoxide, maintained under an argon atmosphere and with stirring. The reaction medium was maintained stirring for 3 days at a temperature in the region of 20° C. and then poured into 500 cm³ of dichloromethane. 100 cm³ of a saturated aqueous potassium carbonate solution were then added, with vigorous stirring, until a pH in the region of 7 was obtained. After stirring for 10 minutes, the organic phase was separated by decantation and the aqueous phase was reextracted 2 times with 250 cm³ of dichloromethane. The organic phases were pooled, washed 3 times with 100 cm³ of distilled water, dried over magnesium sulphate, filtered and concentrated to dryness under reduced pressure (2.7 kPa) at 40° C. 9.5 g of a pale yellow oil were obtained which were purified by chromatography on 250 g of silica (0.063–0.4 mm) contained in a column 3 cm in diameter [eluent: dichloromethane/methanol (99-1 by volume)], collecting 50-cm³ fractions. The fractions containing only the desired product were pooled and concentrated to dryness under reduced pressure (2.7 kPa) at 40° C. 3.01 g of 4α-acetoxy-2α-benzoyloxy-5↑,20-epoxy-1β-hydroxy-10β-methoxyacetoxy-7β-methylthiomethoxy-9-oxo-11-taxen-13α-yl (2R,4S,5R)-3-tert-butoxycarbonyl-2-(4-methoxyphenyl)-4-phenyl-1,3-oxazolidine-5-carboxylate were thereby obtained in the form of a white foam.

4α-acetoxy-2α-benzoyloxy-5β,20-epoxy-1β,7β-dihydroxy-10β-methoxyacetoxy-9-oxo-11-taxen-13α-yl (2R,4S,5R)-3-tert-butoxycarbonyl-2-(4-methoxyphenyl)-4-phenyl-1,3-oxazolidine-5-carboxylate were prepared in the following manner:

220 cm³ of the triethylamine-hydrofluoric acid complex (1–3 by mol) were added dropwise, at a temperature in the region of 0° C., to a solution of 20 g of 4α-acetoxy-2α-benzoyloxy-5β,20-epoxy- 7β-triethylsilyloxy-15-hydroxy-10β-methoxyacetoxy-9-oxo-11-taxen-13α-yl (2R,4S,5R)-3-tert-butoxycarbonyl-2-(4-methoxyphenyl)-4-phenyl-1,3-oxazolidine-5-carboxylate in 200 cm³ of anhydrous dichloromethane, maintained under an argon atmosphere and with stirring. The reaction medium was then heated up to a temperature in the region of 20° C., maintained for 3 hours at this temperature and poured into 4 liters of an aqueous saturated sodium hydrogen carbonate solution. The pH of the reaction medium was thus brought to about 7. After stirring for 10 minutes, the organic phase was separated by decantation and the aqueous phase was extracted 2 times with 100 cm³ of dichloromethane. The organic phases were pooled, washed with 100 cm³ of distilled water, dried over magnesium sulphate, filtered and concentrated to dryness under reduced pressure (2.7 kPa) at 40° C. 17.4 g of 4α-acetoxy-2α-benzoyloxy-5β,20-epoxy-1β,7β-dihydroxy-10β-methoxyacetoxy-9-oxo-11-taxen-13α-yl (2R,4S,5R)-3-tert-butoxycarbonyl-2-(4-methoxyphenyl)-4-phenyl-1,3-oxazolidine-5-carboxylate were thereby obtained in the form of a white foam.

4α-acetoxy-2α-benzoyloxy-5β,20-epoxy-7β-triethylsilyloxy-1β-hydroxy-10β-methoxyacetoxy-9-oxo-11-taxen-13α-yl (2R,4S,5R)-3-tert-butoxycarbonyl-2-(4-methoxyphenyl)-4-phenyl-1,3-oxazolidine-5-carboxylate were prepared under the conditions described in international application PCT WO 95/11241.

EXAMPLE 2

A solution of 40 mg of 4α-acetoxy-2α-benzoyloxy-5β,20-epoxy-1β-hydroxy-7β,10α-dimethoxy-9-oxo-11-taxen-13α-yl (2R,4S,5R)-3-tert-butoxycarbonyl-2-(4-methoxyphenyl)-4-phenyl-1,3-oxazolidine-5-carboxylate in 0.84 cm³ of a 0.1N hydrochloric acid ethanolic solution containing 1% water was stirred for 2 hours at a temperature in the region of 20° C. and then supplemented with 1 cm³ of a saturated aqueous sodium hydrogen carbonate solution and with 2 cm³ of dichloromethane. The mixture was stirred for 5 minutes at a temperature in the region of 20° C. and the organic phase was separated by decantation. The aqueous phase is reextracted 2 time with 2 cm³ of dichloromethane. The organic phases were pooled, dried over magnesium sulphate, filtered and concentrated to dryness under reduced pressure (2.7 kPa) at 40° C. 38 mg of a white foam were obtained which are purified by chromatography on a silica gel plate [gel 1 mm thick, 1 plate of 20×20 cm, eluent: dichloromethane/methanol (95-5 by volume)]. After locating, using UV rays, the zone corresponding to the desired product adsorbed, this zone was scraped off and the silica recovered was washed on sintered glass 10 times with 2 cm³ of ethyl acetate. The filtrates were pooled and concentrated to dryness under reduced pressure (2.7 kPa) at 20° C. 14 mg of 4α-acetoxy-2α-benzoyloxy-5β,20-epoxy-1β-hydroxy-7β,10α-dimethoxy-9-oxo-11-taxen-13α-yl (2R, 3S)-3-tert-butoxycarbonylamino- 2-hydroxy-3-phenylpropionate were thereby obtained in the form of a white foam, the characteristics of which were as follows: —¹H NMR spectrum (400 MHz; CDCl₃; chemical shifts δ in ppm; coupling constants J in Hz): 1.13 (s, 3H:—CH₃ at position 16 or 1 at position 7); 1.27 (s, 3H:—CH₃ at position 16 or 17); 1.39 [s, 9H:—C(CH₃)₃]; 1.72 (s, 3H:—CH₃); 1.76 (s, 1H:—OH at position 1); 1.78 and 2.78 (2 mts, 1H each:—CH₂— at position 6); 2.03 (s, 3H:—CH₃); 2.27 and 2.37 (2dd, J=16 and 9, 1H each:—CH₂— at position 14); 2.38 (s, 3H:—COCH₃); 3.28 (s, 3H:—OCH₃); 3.42 (broad s, 1H:—OH at position 2'); 3.47 (s, 3H:—OCH₃); from 4.15 to 4.25 (mt, 2H:—H at position 3 and —H at position 7); 4.18 and 4.32 (2 d, J=8.5, 1H each:—CH₂— at position 20); 4.52 (broad s, 1H:—H at position 10); 4.64 (mt, 1H:—H at position 2'); 5.01 (broad d, J=10, 1H:—H at position 5); 5.30 (broad d, J=10, 1H:—H at position 3'); 5.45 (d, J=10, 1H:—CONH—); 5.65 (d, J=7.5, 1H:—H at position 2); 6.15 (broad t, J=9, 1H:—H at position 13); from 7.25 to 7.45 (mt, 5H:—C₆H₅ at position 3'); 7.51 [t, J=7.5, 2H:—OCOC₆H₅ (—H at position 3 and H at position 5)]; 7.62 [t, J=7.5, 1H:—OCOC₆H₅(—H at position 4)]; 8.12 [d, J=7.5, 2H:—OCOC₆H₅(—H at position 2 and H at position 6)].

4α-acetoxy-2α-benzoyloxy-5β,20-epoxy-1β-hydroxy-7β,10α-dimethoxy-9-oxo-11-taxen-13α-yl (2R,4S,5R)-3-tert-butoxycarbonyl-2-(4-methoxyphenyl)-4-phenyl-1,3-oxazolidine-5-carboxylate may be prepared in the following manner:

0.5 cm³ of methyl iodide and 3.6 mg of a dispersion at 50% by weight of sodium hydride in mineral oil were added, at a temperature in the region of 0° C., to a solution of 37 mg of 4α-acetoxy-2α-benzoyloxy-5β,20-epoxy-1β,10α-dihydroxy-7β-methoxy-9-oxo-11-taxen-13α-yl (2R,4S,5R)-3-tert-butoxycarbonyl-2-(4-methoxyphenyl)-4-phenyl-1,3-oxazolidine-5-carboxylate in 0.5 cm³ of anhydrous dimethylformamide, maintained under an argon atmosphere and with stirring. The reaction medium was maintained stirring for 30 minutes at a temperature in the region of 0OC and then 10 cm³ of ethyl acetate and 5 cm³ of an aqueous saturated ammonium chloride solution were added. After stirring for 5 minutes, the organic phase was separated by decantation and the aqueous phase was reextracted 2times with 5 cm³ of ethyl acetate. The organic phases were pooled, washed 2 times with 10 cm³ of distilled water, dried over magnesium sulphate, filtered and concentrated to dryness under reduced pressure (2.7 kPa) at 40° C. A white foam was obtained which was purified by chromatography on a silica gel plate [gel 1 mm thick, 1 plate of 20×20 cm, eluent: dichloromethane/methanol (95-5 by volume)]. After locating, using UV rays, the zone corresponding to the desired product adsorbed, this zone was scraped off and the silica recovered was washed on sintered glass 10 times with 2 cm³ of ethyl acetate. The filtrates were pooled and concentrated to dryness under reduced pressure (2.7 kPa) at 20° C. 26 mg of 4α-acetoxy-2α-benzoyloxy-5β,20-epoxy-1β-hydroxy-7β,10α-dimethoxy-9-oxo-11-taxen-13α-yl (2R,4S, 5R)-3-tert-butoxycarbonyl-2-(4-methoxyphenyl)-4-phenyl-1,3-oxazolidine-5-carboxylate were thereby obtained in the form of a white foam.

The new products of general formula (I) in which Z represents a radical of general formula (II) manifest significant inhibitory activity with respect to abnormal cell proliferation, and possess therapeutic properties permitting the treatment of patients having pathological conditions associated with abnormal cell proliferation. The pathological conditions include the abnormal cell proliferation of malignant or non-malignant cells of various tissues and/or organs, comprising, without implied limitation, muscle, bone or connective tissue, the skin, brain, lungs, sex organs, the lymphatic or renal systems, mammary or blood cells, liver, the digestive system, pancreas and thyroid or adrenal glands. These pathological conditions can also include psoriasis, solid tumours, cancers of the ovary, breast, brain, prostate, colon, stomach, kidney or testicles, Kaposi's sarcoma, cholangiocarcinoma, choriocarcinoma, neuroblastoma, Wilms' tumour, Hodgkin's disease, melanoma, multiple myeloma, chronic lymphocytic leukaemia and acute or chronic granulocytic lymphoma. The new products according to the invention are especially useful for the treatment of cancer of the ovary. The products according to the invention may be used to prevent or delay the appearance or reappearance of the pathological conditions, or to treat these pathological conditions.

The products according to the invention may be administered to a patient according to different dosage forms suited to the chosen administration route, which is preferably the parenteral route. Parenteral administration comprises intravenous, intraperitoneal, intramuscular or subcutaneous administration. Intraperitoneal or intravenous administration is more especially preferred.

The present invention also comprises pharmaceutical compositions containing at least one product of general formula (I), in a sufficient amount suitable for use in human or veterinary therapy. The compositions may be prepared according to the customary methods, using one or more pharmaceutically acceptable adjuvants, vehicles or excipients. Suitable vehicles include diluents, sterile aqueous media and various non-toxic solvents. Preferably, the compositions take the form of aqueous solutions or suspensions, injectable solutions which can contain emulsifying agents, colourings, preservatives or stabilizers. However, the compositions may also be provided in the form of tablets, pills, powders or granules which can be administered via the oral route.

The choice of adjuvants or excipients may be determined by the solubility and the chemical properties of the product, the particular mode of administration and good pharmaceutical practice.

For parenteral administration, sterile, aqueous or non-aqueous solutions or suspensions are used. For the preparation of non-aqueous solutions or suspensions, natural vegetable oils such as olive oil, sesame oil or liquid petroleum, or injectable organic esters such as ethyl oleate, may be used. The sterile aqueous solutions can consist of a solution of a pharmaceutically acceptable salt dissolved in water. The aqueous solutions are suitable for intravenous administration provided the pH is appropriately adjusted and the solution is made isotonic, for example with a sufficient amount of sodium chloride or glucose. The sterilization may be carried out by heating or by any other means which does not adversely affect the composition.

It is clearly understood that all the products participating in the compositions according to the invention must be pure and non-toxic in the amounts used.

The compositions can contain at least 0.01% of therapeutically active product. The amount of active product in a composition is such that a suitable dosage can be prescribed. Preferably, the compositions are prepared in such a way that a single dose contains from 0.01 to 1000 mg approximately of active product for parenteral administration.

The therapeutic treatment may be performed concurrently with other therapeutic treatments including antineoplastic drugs, monoclonal antibodies, immunotherapy or radiotherapy or biological response modifiers. The response modifiers include, without implied limitation, lymphokines and cytokines such as interleukins, interferons ($\alpha$, $\beta$ or $\delta$) and TNF. Other chemotherapeutic agents which are useful in the treatment of disorders due to abnormal cell proliferation include, without implied limitation, alkylating agents, for instance nitrogen mustards such as mechlorethamine, cyclophosphamide, melphalan and chlorambucil, alkyl sulphonates such as busulfan, nitrosoureas such as carmustine, lomustine, semustine and streptozocin, triazenes such as dacarbazine, antimetabolites such as folic acid analogues, for instance methotrexate, pyrimidine analogues such as fluorouracil and cytarabine, purine analogues such as mercaptopurine and thioguanine, natural products, for instance vinca alkaloids such as vinblastine, vincristine and vindesine, epipodophyllotoxins such as etoposide and teniposide, antibiotics such as dactinomycin, daunorubicin, doxorubicin, bleomycin, plicamycin and mitomycin, enzymes such as L-asparaginase, various agents such as coordination complexes of platinum, for instance cisplatin, substituted ureas such as hydroxyurea, methylhydrazine derivatives such as procarbazine, adrenocortical suppressants such as mitotane and aminoglutethimide, hormones and antagonists such as adrenocorticosteroids such as prednisone, progestins such as hydroxyprogesterone caproate, methoxyprogesterone acetate and megestrol acetate, oestrogens such as diethylstilboestrol and ethynyloestradiol, antioestrogens such as tamoxifen, and androgens such as testosterone propionate and fluoxymesterone.

The doses used for carrying out the methods according to the invention are those which permit a prophylactic treatment or a maximum therapeutic response. The doses vary according to the administration form, the particular product selected and the features distinctive to the subject to be treated. In general, the doses are those which are therapeutically effective for the treatment of disorders due to abnormal cell proliferation. The products according to the invention may be administered as often as necessary to obtain the desired therapeutic effect. Some patients may respond rapidly to relatively high or low doses, and then require low or zero maintenance doses. Generally, low doses will be used at the beginning of the treatment and, if necessary, increasingly stronger doses will be administered until an optimum effect is obtained. For other patients, it may be necessary to administer maintenance doses 1 to 8 times a day, and preferably 1 to 4 times, according to the physiological requirements of the patient in question. It is also possible that some patients may require the use of only one to two daily administrations.

In man, the doses are generally between 0.01 and 200 mg/kg. For intraperitoneal administration, the doses will generally be between 0.1 and 100 mg/kg, preferably between 0.5 and 50 mg/kg and still more specifically between 1 and 10 mg/kg. For intravenous administration, the doses are generally between 0.1 and 50 mg/kg, preferably between 0.1 and 5 mg/kg and still more specifically between 1 and 2 mg/kg. It is understood that, in order to choose the most suitable dosage, account should be taken of the administration route, the patient's weight, general state of health and age and all the factors which may influence the efficacy of the treatment.

The example which follows illustrates a composition according to the invention.

EXAMPLE 40 mg of the product obtained in Example 1 are dissolved in 1 cm³ of Emulphor EL 620 and 1 cm³ of ethanol, and the solution is then diluted by adding 18 cm³ of physiological saline.

The composition is administered by perfusion over 1 hour by introduction in physiological solution.

We claim:
1. Taxoids of formula I:

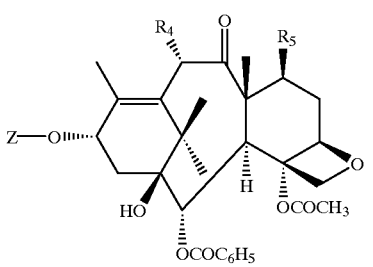

(I)

in which

Z represents a hydrogen atom or a radical of general formula:

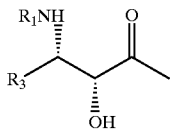

(II)

in which:
R₁ represents a benzoyl radical optionally substituted with one or more identical or different atoms or radicals selected from halogen atoms, alkyl radicals containing 1 to 4 carbon atoms, alkoxy radicals containing 1 to 4 carbon atoms, trifluoromethyl radicals, thenoyl or furoyl radicals, or a radical R₂—O—CO— in which R₂ represents:
an alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 10 carbon atoms, these radicals being optionally substituted with one or more substituents selected from halogen atoms, hydroxyl radicals, alkoxy radicals containing 1 to 4 carbon atoms, dialkylamino radicals in which each alkyl portion contains 1 to 4 carbon atoms, piperidino radicals, morpholino radicals, 1-piperazinyl radicals (optionally substituted at the 4-position with an alkyl radical containing 1 to 4 carbon atoms or with a phenylalkyl radical in which the alkyl portion contains 1 to 4 carbon atoms), cycloalkyl radicals containing 3 to 6 carbon atoms, cycloalkenyl radicals containing 4 to 6 carbon atoms, phenyl radicals (optionally substituted with one or more atoms or radicals chosen from halogen atoms, alkyl radicals containing 1 to 4 carbon atoms, or alkoxy radicals containing 1 to 4 carbon atoms), cyano or carboxyl radicals or alkoxycarbonyl radicals in which the alkyl portion contains 1 to 4 carbon atoms, a phenyl or α- or β-naphthyl radical optionally substituted with one or more atoms or radicals selected from halogen atoms, alkyl radicals containing 1 to 4 carbon atoms, or alkoxy radicals containing 1 to 4 carbon atoms, or a 5-membered aromatic heterocyclic radical, or a saturated heterocyclic radical containing 4 to 6 carbon atoms, optionally substituted with one or more alkyl radicals containing 1 to 4 carbon atoms, R₃ represents an unbranched or branched alkyl radical containing 1 to 8 carbon atoms, an unbranched or branched alkenyl radical containing 2 to 8 carbon atoms, an unbranched or branched alkynyl radical containing 2 to 8 carbon atoms, a cycloalkyl radical containing 3 to 6 carbon atoms, a phenyl or α- or β-naphthyl radical optionally substituted with one or more atoms or radicals chosen from halogen atoms and alkyl, alkenyl, alkynyl, aryl, aralkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, alkylcarbamoyl, dialkylcarbamoyl, cyano, nitro and trifluoromethyl radicals, or a 5-membered aromatic heterocycle containing one or more identical or different hetero atoms selected from nitrogen, oxygen and sulphur atoms and optionally substituted with one or more identical or different substituents chosen from halogen atoms and alkyl, aryl, amino, alkylamino, dialkylamino, alkoxycarbonylamino, acyl, arylcarbonyl, cyano, carboxyl, carbamoyl, alkylcarbamoyl, dialkylcarbamoyl or alkoxycarbonyl radicals, wherein, in the substituents of the phenyl, α- or β-naphthyl and aromatic heterocyclic radicals, the alkyl radicals and the alkyl portions of the other radicals contain 1 to 4 carbon atoms, and the alkenyl and alkynyl radicals contain 2 to 8 carbon atoms, and the aryl radicals are phenyl or α- or β-naphthyl radicals, R₄ represents a hydroxyl radical or an alkoxy radical containing 1 to 6 carbon atoms in an unbranched or branched chain, an alkenyloxy radical containing 3 to 6 carbon atoms in an unbranched or branched chain, an alkynyloxy radical containing 3 to 6 carbon atoms in an unbranched or branched chain, a cycloalkyloxy radical containing 3 to 6 carbon atoms, a cycloalkenyloxy radical containing 3 to 6 carbon atoms, an alkanoyloxy radical in which the alkanoyl portion contains 3 to 6 carbon atoms in an unbranched or branched chain, an alkenoyloxy radical in which the alkenoyl portion contains 3 to 6 carbon atoms in an unbranched or branched chain, an alkynoyloxy radical in which the alkynoyl portion contains 3 to 6 carbon atoms in an unbranched or branched chain, an alkoxyacetyl radical in which the alkyl portion contains 1 to 6 carbon atoms in an unbranched or branched chain, an alkylthioacetyl radical in which the alkyl portion contains 1 to 6 carbon atoms in an unbranched or branched chain or an alkyloxycarbonyloxy radical in which the alkyl portion contains 1 to 6 carbon atoms in an unbranched or branched chain, these radicals being optionally substituted with one or more halogen atoms, an alkoxy radical containing 1 to 4 carbon atoms, an alkylthio radical containing 1 to 4 carbon atoms or a carboxyl radical, an alkyloxycarbonyl radical in which the alkyl portion contains 1 to 4 carbon atoms, a cyano or carbamoyl radical or an N-alkylcarbamoyl or N,N-dialkylcarbamoyl radical in which each alkyl portion contains 1 to 4 carbon atoms or, with the nitrogen atom to which it is linked, forms a saturated 5- or 6-membered heterocyclic radical optionally containing a second hetero atom chosen from oxygen, sulphur and nitrogen atoms, optionally substituted with an alkyl radical containing 1 to 4 carbon atoms or a phenyl radical or a phenylalkyl radical in which the alkyl portion contains 1 to 4 carbon atoms, or alternatively $R_4$ represents a benzoyloxy radical or a heterocyclyl-carbonyloxy radical in which radical the heterocyclic portion represents a 5- or 6-membered aromatic heterocycle containing one or more hetero atoms selected from oxygen, sulphur and nitrogen atoms, $R_5$ represents an alkoxy radical containing 1 to 6 carbon atoms in an unbranched or branched chain optionally substituted with an alkoxy radical containing 1 to 4 carbon atoms, an alkenyloxy radical containing 3 to 6 carbon atoms, an alkynyloxy radical containing 3 to 6 carbon atoms, a cycloalkyloxy radical containing 3 to 6 carbon atoms, a cycloalkenyloxy radical containing 3 to 6 carbon atoms, these radicals being optionally substituted with one or more halogen atoms, an alkoxy radical containing 1 to 4 carbon atoms, an alkylthio radical containing 1 to 4 carbon atoms or a carboxyl radical, an alkyloxycarbonyl radical in which the alkyl portion contains 1 to 4 carbon atoms, a cyano or carbamoyl radical or an N-alkylcarbamoyl or N,N-dialkylcarbamoyl radical in which each alkyl portion contains 1 to 4 carbon atoms or, with the nitrogen atom to which it is linked, forms a saturated 5- or 6-membered heterocyclic radical optionally containing a second hetero atom selected from oxygen, sulphur and nitrogen atoms, optionally substituted with an alkyl radical containing I to 4 carbon atoms or a phenyl radical or a phenylalkyl radical in which the alkyl portion contains 1 to 4 carbon atoms.

2. A taxoid according to claim 1, wherein Z represents a hydrogen atom or a radical of general formula (II) in which $R_1$ represents a benzoyl radical or a radical $R_2$—O—CO— in which $R_2$ represents a tert-butyl radical and $R_3$ represents an alkyl radical containing 1 to 6 carbon atoms, an alkenyl radical containing 2 to 6 carbon atoms, a cycloalkyl radical containing 3 to 6 carbon atoms, a phenyl radical optionally substituted with one or more identical or different atoms or radicals selected from halogen atoms and alkyl, alkoxy, dialkylamino, acylamino, alkoxycarbonylamino and trifluoromethyl radicals, or a 2- or 3-furyl, 2- or 3-thienyl or 2-, 4- or 5-thiazolyl radical, and $R_4$ represents a hydroxyl radical or an unbranched or branched alkyloxy radical containing 1 to 6 carbon atoms and $R_5$ represents an unbranched or branched alkyloxy radical containing 1 to 6 carbon atoms.

3. A taxoid according to claim 1, wherein Z represents a hydrogen atom or a radical of general formula (II) in which $R_1$ represents a benzoyl radical or a radical $R_2$—O—CO— in which $R_2$ represents a tert-butyl radical and $R_3$ represents an isobutyl, isobutenyl, butenyl, cyclohexyl, phenyl, 2-furyl, 3-furyl, 2-thienyl, 3-thienyl, 2-thiazolyl, 4-thiazolyl or 5-thiazolyl radical, $R_4$ represents a hydroxyl radical or a methoxy radical and $R_5$ represents a methoxy radical.

4. A process for the preparation of a taxoid according to claim 1, wherein Z represents a radical of general formula (II), said process comprising esterifying a product of general formula Ill:

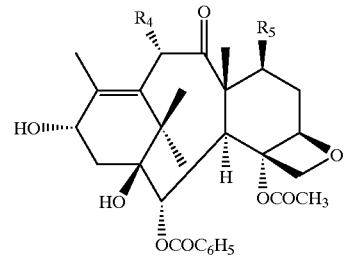

(III)

in which $R_4$ and $R_5$ are defined in claim 1 by means of an acid of general formula IV:

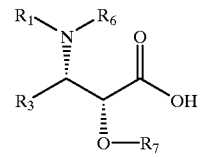

(IV)

in which $R_1$ and $R_3$ are defined in claim 1 and either $R_6$ represents a hydrogen atom and $R_7$ represents a group protecting the hydroxyl function, or $R_6$ and $R_7$ together form a saturated 5- or 6-membered heterocycle, or of a derivative of this acid, to obtain an ester of general formula V:

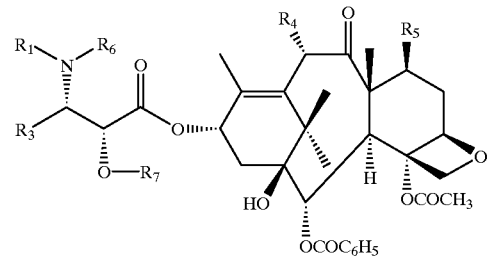

(V)

in which $R_1$, $R_3$, $R_4$, $R_5$, $R_6$ and $R_7$ are defined as above, and the protective groups represented by $R_7$ and/or $R_6$ and $R_7$ are replaced with hydrogen atoms and, optionally, the $R_4$ radical is replaced with a hydroxyl radical.

5. The process according to claim 4, wherein the esterification is carried out by means of an acid of general formula (IV), in the presence of a condensing agent and of an activating agent, in an organic solvent at a temperature of between −10 and 90° C.

6. The process according to claim 4, wherein the esterification is carried out by means of an acid of general formula (IV) in the form of a symmetric anhydride, working in the presence of an activating agent, in an organic solvent at a temperature of between 0 and 90° C.

7. The process according to claim 4, wherein the esterification is carried out using the acid of general formula (IV) in the form of a halide or in the form of a mixed anhydride with an aliphatic or aromatic acid, optionally prepared in situ, in the presence of a base, working in an organic solvent at a temperature of between 0 and 80° C.

8. The process according to claim 4, wherein the protective groups $R_7$ and/or $R_6$ and $R_7$ are replaced with hydrogen atoms, according to their nature, in the following manner:
1) When $R_6$ represents a hydrogen atom and $R_7$ represents a group protecting the hydroxyl function, the replacement of the protective groups with hydrogen atoms is carried out by means of an inorganic acid or an organic acid, used alone or in the form of a mixture, working in an organic solvent chosen from alcohols, ethers, esters, aliphatic hydrocarbons, halogenated aliphatic hydrocarbons, aromatic hydrocarbons and nitrites, at a temperature of between −10 and 60° C.,
2) When $R_6$ and $R_7$ together form a saturated 5- or 6-membered heterocycle of general formula:

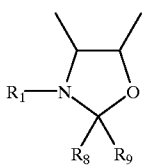

(VI)

in which $R_1$ is defined as above, $R_8$ and $R_9$, which are identical or different, represent a hydrogen atom, an alkyl radical containing 1 to 4 carbon atoms, an aralkyl radical in which the alkyl portion contains 1 to 4 carbon atoms and the aryl portion represents a phenyl radical optionally substituted with one or more alkoxy radicals containing 1 to 4 carbon atoms, or an aryl radical representing a phenyl radical optionally substituted with one or more alkoxy radicals containing 1 to 4 carbon atoms, $R_8$ represents an alkoxy radical containing 1 to 4 carbon atoms or a trihalomethyl radical or a phenyl radical substituted with a trihalomethyl radical and $R_9$ represents a hydrogen atom, or
$R_8$ and $R_9$ together form, with the carbon atom to which they are linked, a ring having 4 to 7 members, the replacement of the protective group formed by $R_6$ and $R_7$ with hydrogen atoms is carried out, according to the meanings of $R_1$, $R_8$ and $R_9$, working in the following manner:
a) When $R_1$ represents a tert-butoxycarbonyl radical, $R_8$ and $R_9$, which are identical or different, represent an alkyl radical or an aralkyl or aryl radical, either $R_8$ represents a trihalomethyl radical or a phenyl radical substituted with a trihalomethyl radical, and $R_9$ represents a hydrogen atom, or $R_8$ and $R_9$ together form a 4- to 7-membered ring, the ester of general formula (V) is treated with an inorganic or organic acid, optionally in an organic solvent such as an alcohol, to give the product of general formula VII:

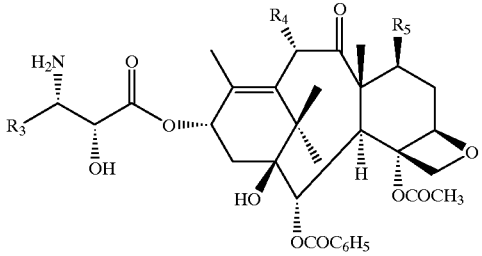

(VII)

in which $R_3$, $R_4$ and $R_5$ are defined as above, which is acylated by means of benzoyl chloride in which the phenyl ring is optionally substituted, thenoyl chloride, furoyl chloride or a product of general formula VII:

$$R_2-O-CO-X \qquad (VIII)$$

in which $R_2$ is defined as above and X represents a halogen atom or a residue $-O-R_2$ or $-O-CO-O-R_2$, to obtain a taxoid according to claim 1 wherein Z represents a radical of general formula (II),
b) When $R_1$ represents an optionally substituted benzoyl radical, a thenoyl or furoyl radical or a radical $R_2O-CO-$ in which $R_2$ is defined as above, $R_8$ represents a hydrogen atom or an alkoxy radical containing 1 to 4 carbon atoms or a phenyl radical substituted with one or more alkoxy radicals containing 1 to 4 carbon atoms and $R_9$ represents a hydrogen atom, the protective group formed by $R_6$ and $R_7$ is replaced with hydrogen atoms is carried out in the presence of an inorganic acid or an organic acid, used alone or in the form of a mixture, in a stoichiometric or catalytic quantity, working in an organic solvent chosen from alcohols, ethers, esters, aliphatic hydrocarbons, halogenated aliphatic hydrocarbons and aromatic hydrocarbons at a temperature of between −10 and 60° C.

9. A process for the preparation of a taxoid according to claim 1, wherein Z represents a hydrogen atom or a radical of general formula (II), wherein a product of general formula IX:

$$R'_4-X_1 \qquad (IX)$$

in which $R'_4$ is such that $R'_4-O$ is identical to $R_4$ defined in claim 1 and $X_1$ represents a halogen atom, is reacted with a product of general formula X:

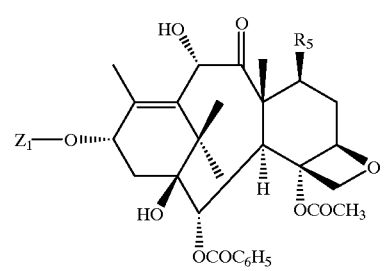

(X)

in which $R_5$ is defined as in claim 1 and $Z_1$ represents a hydrogen atom, a group protecting the hydroxyl function or a radical of general formula XI:

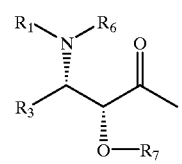

(XI)

in which $R_1$ and $R_3$ are defined as in claim 1, and $R_6$ represents a hydrogen atom and $R_7$ represents a group protecting the hydroxyl function, or
$R_6$ and $R_7$ together form a saturated 5- or 6-membered heterocycle, and then the protective groups represented or carried by $Z_1$ are optionally replaced under the conditions described in claim 8.

10. The process according to claim 9, wherein the product of general formula (IX) is reacted with the product of general formula (X), after metalation of the hydroxyl function at the 10-position by means of an alkali metal hydride, an alkali metal amide or an alkali metal alkylide, working in an organic solvent chosen from dimethylformamide or tetrahydrofuran, at a temperature of between 0 and 50° C.

11. 4α-acetoxy-2α-benzoyloxy-5β,20-epoxy-1β, α-dihydroxy-7β-methoxy-9-oxo-11-taxen-13α-yl (2R,3S)-3-tert-butoxycarbonylamino-2-hydroxy-3-phenylpropionate.

12. 4α-acetoxy-2α-benzoyloxy-5β,20-epoxy-1β-hydroxy-7β,10α-dimethoxy-9-oxo-11-taxen-13α-yl (2R,3S)-3-tert-butoxycarbonylamino-2-hydroxy-3-phenylpropionite.

13. A pharmaceutical composition comprising at least one taxoid according to claim 1, wherein Z represents a radical of general formula (II), in combination with one or more pharmaceutically acceptable diluents or adjuvants and optionally one or more compatible and pharmacologically active compounds.

14. A pharmaceutical composition comprising at least one compound according to claim 11 in combination with one or more pharmaceutically acceptable diluents or adjuvants and optionally one or more compatible and pharmacologically active compounds.

15. A pharmaceutical composition comprising at least one compound according to claim 12 in combination with one or more pharmaceutically acceptable diluents or adjuvants and optionally one or more compatible and pharmacologically active compounds.

16. The taxoid according to claim 1, wherein, in the definition of $R_1$, the 5-membered aromatic heterocyclic radical is a furyl or thienyl radical.

17. The process according to claim 4, wherein $R_4$ represents a group protecting the hydroxyl function.

18. The process according to claim 17, wherein said group protecting the hydroxyl function is selected from alkoxyacetyl radicals.

* * * * *